United States Patent
Rebellino

(10) Patent No.: US 12,310,801 B2
(45) Date of Patent: May 27, 2025

(54) APPARATUS FOR DELIVERING BIOPSY CAVITY MARKER

(71) Applicant: Devicor Medical Products, Inc., Cincinnati, OH (US)

(72) Inventor: Jordan Rebellino, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 808 days.

(21) Appl. No.: 17/333,159

(22) Filed: May 28, 2021

(65) Prior Publication Data
US 2021/0282888 A1    Sep. 16, 2021

Related U.S. Application Data

(63) Continuation of application No. PCT/US2019/066442, filed on Dec. 16, 2019.
(Continued)

(51) Int. Cl.
*A61B 90/00* (2016.01)
*A61B 10/00* (2006.01)
(Continued)

(52) U.S. Cl.
CPC .......... *A61B 90/39* (2016.02); *A61B 10/0041* (2013.01); *A61B 17/3468* (2013.01);
(Continued)

(58) Field of Classification Search
CPC ................ A61B 90/39; A61B 17/3468; A61B 2090/0807; A61B 2090/3987; A61B 2017/00367; A61B 2017/0046
See application file for complete search history.

(56) References Cited

U.S. PATENT DOCUMENTS

| 6,083,524 A | 7/2000 | Sawhney et al. |
| 6,162,241 A | 12/2000 | Coury et al. |

(Continued)

FOREIGN PATENT DOCUMENTS

DE    102015003600 A    3/2015

OTHER PUBLICATIONS

European Communication dated Jan. 4, 2024 for Application No. 19853258.2, 6 pages.
(Continued)

*Primary Examiner* — Baisakhi Roy
(74) *Attorney, Agent, or Firm* — FROST BROWN TODD LLP

(57) ABSTRACT

A marker delivery device including a handle assembly, a delivery catheter, and a connection interface. The handle assembly has an upper push rod positioned within the handle assembly. The upper push rod is adapted to translate inside the handle assembly. The delivery catheter is adapted to be inserted into a biopsy site. Also, the delivery catheter has a discharge opening containing a marker and the delivery catheter has a lower push rod positioned inside of the delivery catheter. The lower push rod is configured to engage the upper push rod and the lower push rod is adapted to deploy the marker from the delivery catheter into the biopsy site through the discharge opening with the translation of the upper push rod. The connection interface is configured to removably attach the handle assembly with the delivery catheter and the upper push rod with the lower push rod.

15 Claims, 9 Drawing Sheets

Related U.S. Application Data

(60) Provisional application No. 62/780,630, filed on Dec. 17, 2018.

(51) Int. Cl.
*A61B 17/34* (2006.01)
*A61B 17/00* (2006.01)

(52) U.S. Cl.
CPC .............. *A61B 2017/00367* (2013.01); *A61B 2017/0046* (2013.01); *A61B 2090/0807* (2016.02); *A61B 2090/3908* (2016.02); *A61B 2090/3925* (2016.02); *A61B 2090/3987* (2016.02)

(56) References Cited

U.S. PATENT DOCUMENTS

| | | |
|---|---|---|
| 6,270,464 B1 | 8/2001 | Fulton, III et al. |
| 6,356,782 B1 | 3/2002 | Sirimanne et al. |
| 6,605,294 B2 | 8/2003 | Sawhney |
| 8,600,481 B2 | 12/2013 | Sirimanne et al. |
| 8,939,910 B2 | 1/2015 | Fisher |
| 10,010,326 B2 | 7/2018 | Sato |
| 2003/0093029 A1* | 5/2003 | McGuckin, Jr. .......................... A61M 25/09041 604/525 |
| 2005/0272975 A1* | 12/2005 | McWeeney ............ A61B 1/307 600/172 |
| 2006/0009858 A1* | 1/2006 | Levine .................. A61F 5/0089 623/23.65 |
| 2008/0125766 A1 | 5/2008 | Lubock et al. |
| 2010/0175693 A1* | 7/2010 | Wondka ............ A61B 17/12104 128/200.24 |
| 2012/0065542 A1* | 3/2012 | Hibner ............... A61B 10/0275 600/567 |
| 2012/0143029 A1* | 6/2012 | Silverstein ........... A61B 8/0891 600/374 |
| 2012/0289772 A1* | 11/2012 | O'Connell ............. A61B 34/20 128/200.24 |
| 2017/0014115 A1* | 1/2017 | Rafiee ...................... A61F 2/88 |
| 2018/0008248 A1* | 1/2018 | Rafiee ............. A61B 17/12145 |
| 2018/0028339 A1* | 2/2018 | Loper .................. A61F 5/0089 |
| 2018/0036511 A1* | 2/2018 | Ryan ................. A61M 25/0147 |
| 2019/0083262 A1* | 3/2019 | Hariton ................. A61F 2/2445 |
| 2021/0196251 A1* | 7/2021 | Dull .................. A61M 25/0102 |

OTHER PUBLICATIONS

International Search Report and Written Opinion dated Apr. 23, 2020 for Application No. PCT/US2019/066442, 16 pages.

* cited by examiner

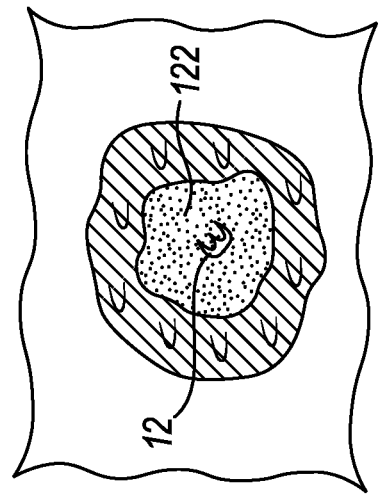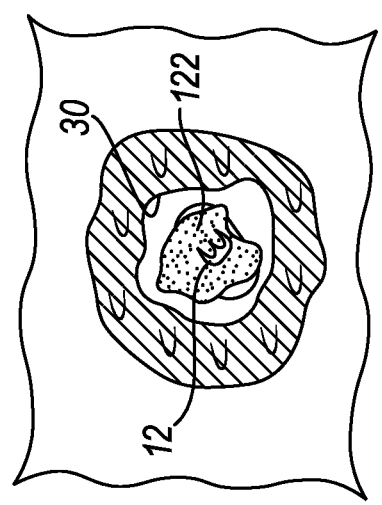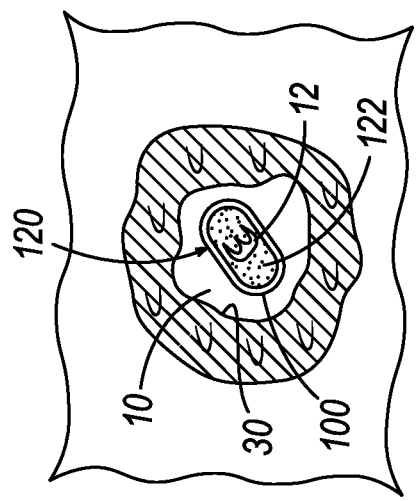

APPARATUS FOR DELIVERING BIOPSY CAVITY MARKER

PRIORITY

This application is a continuation of International Application Number PCT/US2019/066442, filed on Dec. 16, 2019, which claims priority to U.S. Provisional Patent App. 62/780,630 entitled "Apparatus for Delivering Biopsy Cavity Marker," filed on Dec. 17, 2018, the disclosure of which is incorporated by reference herein.

BACKGROUND

A number of patients will have breast biopsies because of irregular mammograms and palpable abnormalities. Biopsies can include surgical excisional biopsies and stereotactic and ultrasound guided needle breast biopsies. In the case of image directed biopsy, the radiologist or other physician may take a small sample of the irregular tissue for laboratory analysis. If the biopsy proves to be malignant, additional surgery (e.g., a lumpectomy or a mastectomy) may be required. In the case of needle biopsies, the patient may return to the radiologist a day or more later, and the biopsy site (the site of the lesion) may need to be relocated in preparation for the surgery. An imaging system, such as ultrasound, magnetic resonance imaging (MRI) or x-ray may be used to locate the biopsy site. In order to assist the relocation of the biopsy site, a marker may be placed at the time of the biopsy.

The use of markers in connection with biopsy procedures to mark the location where the biopsied tissue was removed is described in the following US patents: U.S. Pat. No. 6,083,524, "Polymerizable biodegradable polymers including carbonate or dioxanone linkages," issued Jul. 4, 2000; U.S. Pat. No. 6,162,241, "Hemostatic tissue sealants," issued Dec. 4, 2000; U.S. Pat. No. 6,270,464, "Biopsy localization method and device," issued Aug. 7, 2001; U.S. Pat. No. 6,356,782, "Subcutaneous cavity marking device and method," issued Mar. 12, 2002; U.S. Pat. No. 6,605,294, "Methods of using in situ hydration of hydrogel articles for sealing or augmentation of tissue or vessels," issued Aug. 12, 2003; U.S. Pat. No. 8,600,481, "Subcutaneous cavity marking device," issued Dec. 3, 2013 and U.S. Pat. No. 8,939,910, "Method for enhancing ultrasound visibility of hyperechoic materials", issued Jan. 27, 2015. All of these US patents are incorporated by reference in their entirety.

During placement of a marker at a biopsy site, certain marker delivery devices may be used. Such devices can be used in connection with other biopsy devices or peripheral equipment. For instance, in a stereotactic biopsy procedure, a biopsy device can be guided with the use of x-ray visualization. Such x-ray visualization can be provided in a variety of configurations. However, in many configurations, various visualization related components operate in close proximity with the biopsy device. Meanwhile, marking may be performed using the biopsy device, such that a marker delivery device is inserted directly into the biopsy device.

In some contexts, one or more components of the marker delivery device may physically obstruct or otherwise interfere with one or more components related to x-ray visualization. For instance, in some configurations an x-ray source can be configured to physically sweep in an arc in a region adjacent to the biopsy device. In some context, a marker delivery device protruding from the biopsy device can be located within this region and thus physically obstruct the x-ray source or otherwise interfere. Accordingly, it may be desirable to incorporate features into a marker delivery device to improve use of the marker delivery device with other components associated with a biopsy procedure.

While several systems and methods have been made and used for marking a biopsy site, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

FIGS. 1A, 1B, and 1C show exemplary aspects of placement of a biopsy site marker, in accordance with aspects of the present disclosure;

Figure 2:
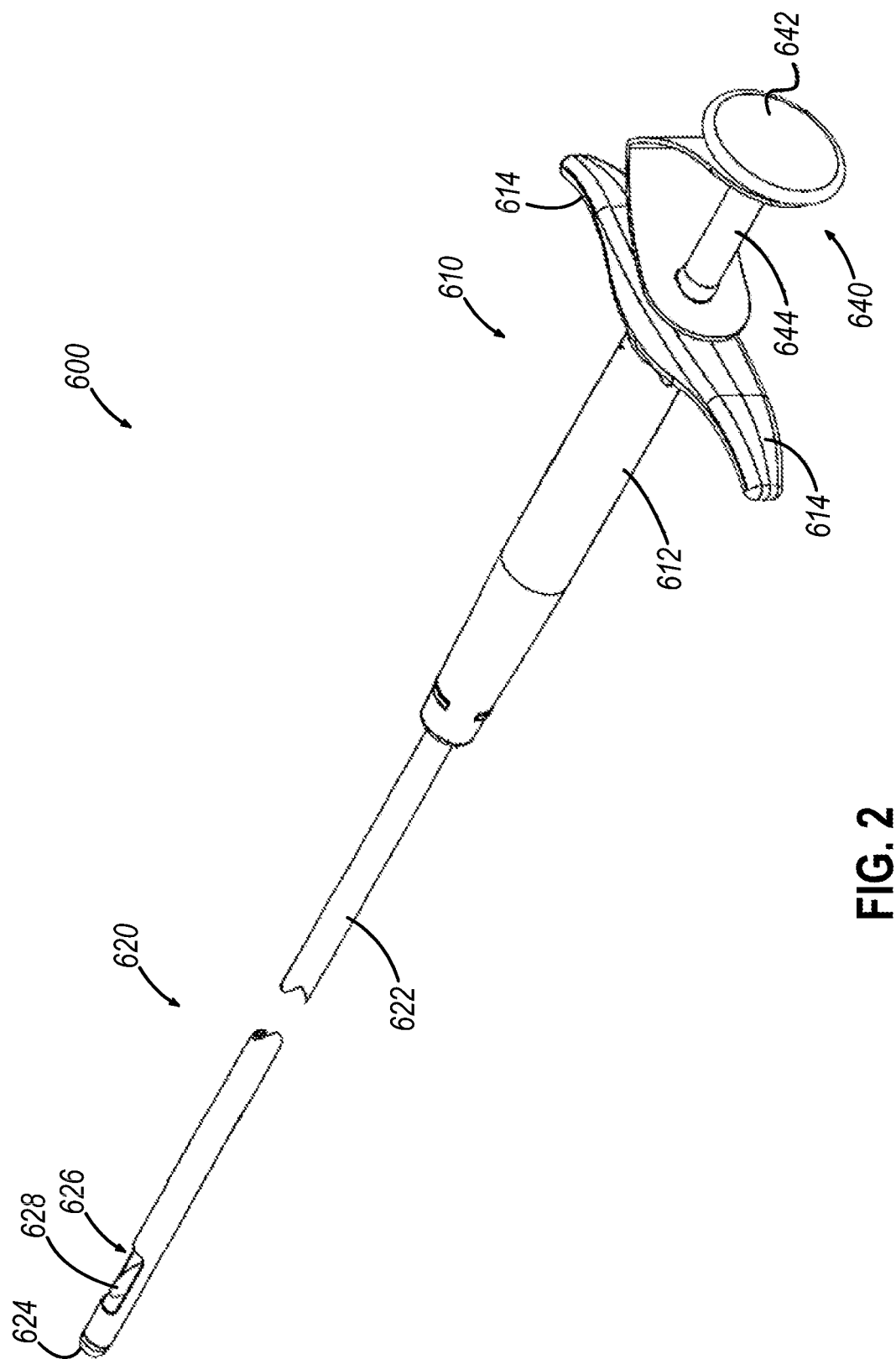
FIG. 2 depicts a perspective view of an exemplary marker delivery device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It may be beneficial to be able to mark the location or margins of a lesion, whether temporarily or permanently, prior to or immediately after removing or sampling it. Marking prior to removal may help to ensure that the entire lesion is excised, if desired. Alternatively, if the lesion were inadvertently removed in its entirety, marking the biopsy site immediately after the procedure would enable reestablishment of its location for future identification.

Once a marker is positioned at a biopsy site, it may be desirable to ensure the handle assembly does not collide with other equipment near the marker delivery device. During the post-marking imaging sequence of the breast biopsy procedure, the handle assembly has a substantial chance of collision with upright x-ray tube heads, as well as several other pieces of equipment. Additionally, the handle assembly may be impacted by the operator while after insertion. It may also be desirable to allow for separation of the handle assembly and the cannula assembly. For instance, the cannula assembly and the handle assembly may be disposable or interchangeable, and maybe separated during the breast biopsy procedure. Thus, it is generally desirable for the marker delivery device maintain the ability to detach the handle assembly from the cannula assembly.

I. EXEMPLARY MARKER

Aspects presented herein relate to devices and procedures for the delivery of a marker for percutaneously marking a biopsy cavity (10) having surrounding tissue (30), as shown in FIGS. 1A-1C. For instance, as seen in FIG. 1A, a marker (100) may be initially placed in the biopsy cavity (10) to facilitate relocation of the biopsy site. Marker (100) may comprise a carrier (120) and a marker element (12). Carrier (120) generally includes a bioabsorbable marker material (122). Thus, carrier (120) is generally configured for absorption into a patient after placement of marker (100) within the biopsy cavity (10). In some examples, carrier (120) can include a plurality of microbubbles to enhance visualization of carrier (120) under ultrasound. Such bubbles may be generally desirable to provide enhanced reflection of ultrasonic radiation from the interior and exterior of marker (100). Marker material (122) is generally bioabsorbable such that marker material (122) may be generally absorbed into the patient's tissue over time. In the present example, marker material (122) comprises a hydrogel that is initially in a dehydrated state. Although a hydrogel is used in the present example, it should be understood that in other examples marker material (122) may comprise other known bioabsorbable materials In the present example, marker (100) further includes a marker element (12) that is generally not bioabsorbable. Marker element (12) may comprise a radiopaque or echogenic marker embedded within the bioabsorbable marker material (122) of carrier (120). For instance, marker element (12) may comprise metal, hard plastic, or other radiopaque or hyperechoic materials known to those of ordinary skill in the art in view of the teachings herein. In other examples, marker (100) may be formed without a marker element (12). In still other examples, marker (100) may be formed with only marker element (12) such that carrier (120) is omitted and marker element (12) is in a "bare" form. In other words, in some examples marker (100) is formed of only carrier (120) as a bare clip.

Marker material (122) is generally expandable once disposed within a patient at a biopsy site. As shown in FIGS. 1B and 1C, the initially dehydrated marker material (122) may absorb fluid from the surrounding tissue (30) into which it is inserted. In response to this absorption of fluid, maker material (122) may swell, thereby permitting carrier (120) to fill a cavity formed at a biopsy site by removal of tissue samples during a biopsy procedure. Biodegradable materials may be particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition.

Marker (100) may be inserted into the body either surgically via an opening in the body cavity (30), or through a minimally invasive procedure using such devices as a catheter, introducer or similar type insertion device. Marker (100) may be delivered immediately after removal of the tissue specimen using the same device used to remove the tissue specimen itself. Follow-up noninvasive detection techniques, such as x-ray mammography or ultrasound may then be used by the physician to identify, locate, and monitor the biopsy cavity site over a period of time via marker (100).

Marker (100) of the present example is large enough to be readily visible to a clinician under x-ray or ultrasonic viewing, for example; yet small enough to be able to be percutaneously deployed into the biopsy cavity and to not cause any difficulties with the patient. Although examples are described in connection with treatment and diagnosis of breast tissue, aspects presented herein may be used for markers in any internal, tissue, e.g., in breast tissue, lung tissue, prostate tissue, lymph gland tissue, etc.

II. EXEMPLARY METHOD FOR DEPOSITING A MARKER OR MARKER ELEMENT INTO TISSUE

FIG. 2 shows an exemplary marker delivery device (600) that can be used in connection with marker (100) described above after formation of marker element (12). Marker delivery device (600) generally includes a handle assembly (610), a delivery catheter (620), and a push rod (640). Handle assembly (610) is generally configured to provide a grip for an operator to readily manipulate marker delivery device (600). In the present example, handle assembly (610) includes a body (612) and a pair of grip arms (614) extending outwardly from body (612). Each grip arm (614) is generally shaped to receive one or more fingers of an operator such that operator may readily manipulate marker delivery device (600).

Delivery catheter (620) extends distally from body (612) of handle assembly (610). Delivery catheter (620) includes an elongate cannula (622) that is distally closed by a blunt distal portion (624). Proximally of distal portion (624), cannula (622) defines a lateral aperture (626). As will be described in greater detail below, lateral aperture (626) is generally configured to permit marker (100) and/or marker element (12) to be ejected from delivery catheter (620).

Delivery catheter (620) further includes a ramp portion (628) disposed within cannula (622) adjacently relative to lateral aperture (626). Ramp portion (628) is generally configured to hold marker (100) and/or marker element (12) within delivery catheter (620), thereby preventing inadvertent ejection of marker (100) and/or marker element (12). As will be described in greater detail below, ramp portion (628) is also generally configured to eject marker (100) and/or marker element (12) laterally out of lateral aperture (626) when an operator desires to deliver marker (100) and/or marker element (12) to a biopsy site.

Push rod (640) is generally configured to manipulate marker (100) and/or marker element (12) to selectively eject marker (100) and/or marker element (12). Push rod (640) includes a button portion (642) and an elongate rod portion (644). Button portion (642) is disposed proximally of handle assembly (610) such that button portion (642) is readily accessible to an operator when gripping marker delivery device (600) via grip arms (614). As will be understood, button portion (642) is generally configured to be manipulated by an operator to drive rod portion (644) distally and thereby eject marker (100) and/or marker element (12) from marker delivery device (600).

Rod portion (644) extends distally from button portion (642). In particular, rod portion (644) extends distally into handle assembly (610). Although not shown, it should be understood that rod portion (644) additionally extends through handle assembly (610) and into cannula (622) of delivery catheter (620). This permits a distal portion of rod portion (644) to be positioned adjacent to lateral aperture (626) to thereby drive marker (100) and/or marker element (12) out of lateral aperture (626).

In an exemplary use, marker element (12) is formed from marker material (13) using the methods known in the art. After formation of marker element (12) it should be understood that marker element (12) is coated with coating material (202) such that marker element (12) will be readily visible under ultrasonic visualization via the microspheres disposed within coating material (202). The coated marker element (12) can next be used without any additional coating or carrier similar to carrier (120) described above (e.g., a "bare" marker). Alternatively, in some examples, marker element (12) undergoes additional steps to dispose marker element (12) within carrier (120) to form marker (100).

Regardless of whether marker element (12) is used in the bare condition or is disposed within carrier (120), the completed marker (100) is next loaded into marker delivery device (600). In the present example, marker (100) may be loaded into marker delivery device (600) through lateral aperture (626) of delivery catheter (620). After loading, marker (100) is held in position by ramp portion (628) and rod portion (644) of push rod (640) is disposed proximally of marker (100).

Figure 3:
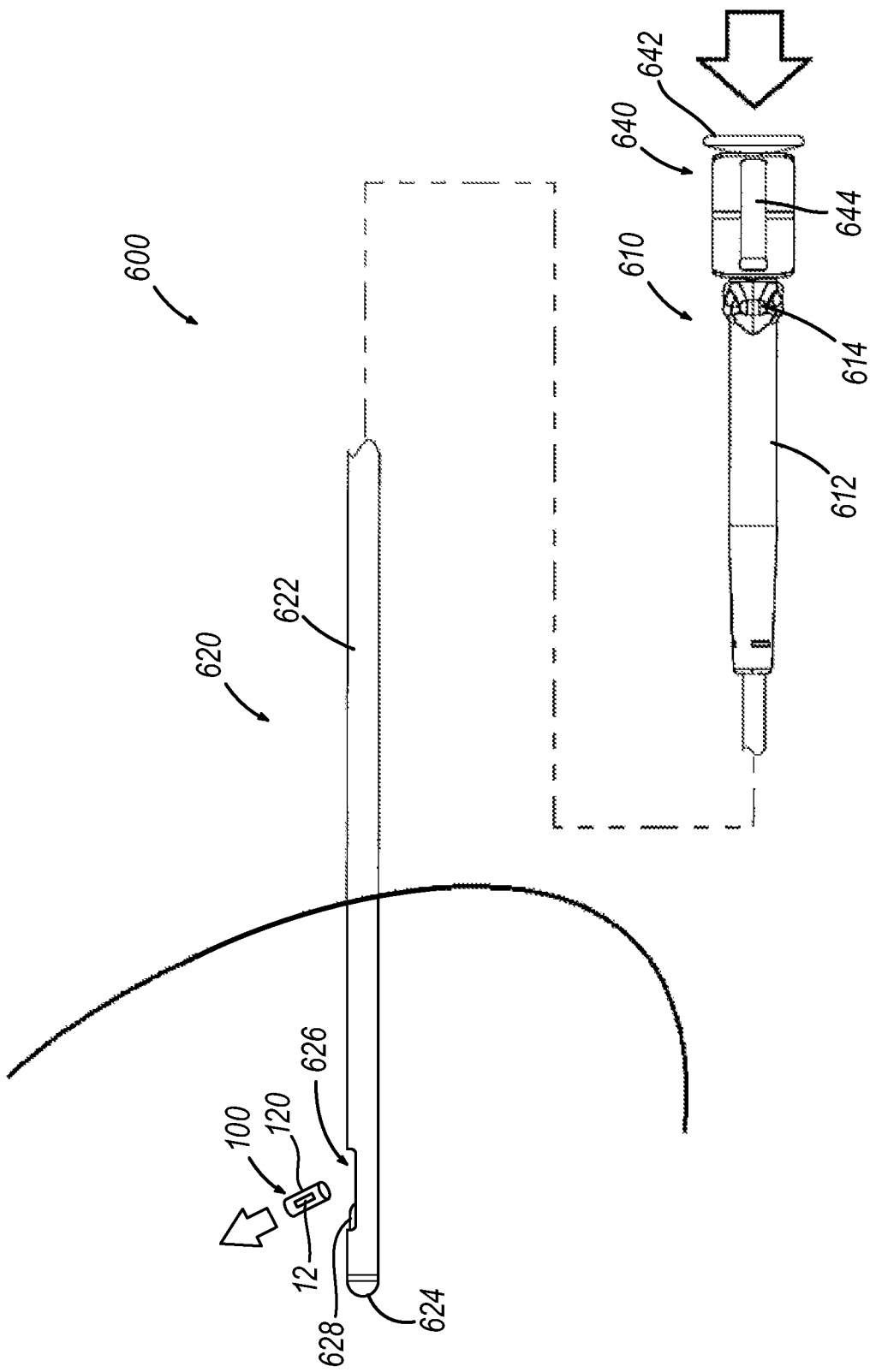
FIG. 3 depicts a side elevational view of the marker delivery device of FIG. 2 being used to deploy a biopsy site marker at a biopsy site.

Once marker (100) is loaded within marker delivery device (600), marker delivery device (600) is ready for insertion into a patient to deploy marker (100) at a biopsy site. As can be seen in FIG. 3, the deployment process starts with insertion of delivery catheter (620) into a patient. Although delivery catheter (620) is shown in the present example as being inserted directly into a patient, it should be understood that in other examples delivery catheter (620) can be inserted into a patient indirectly via other instruments. For instance, in some examples a biopsy device can be used for insertion of delivery catheter (620). In such examples, the biopsy device can include various access ports to permit delivery catheter (620) to be inserted into a needle of the biopsy device. The needle of the biopsy device is then used for insertion of delivery catheter (620) and subsequent delivery of marker (100).

Once delivery catheter (620) is disposed within a patient as desired, an operator may deploy marker (100) at the biopsy site. As seen in FIG. 3, an operator can deploy marker (100) by pressing button portion (642) of push rod (640). This causes rod portion (644) of push rod (640) to advance within cannula (622) of delivery catheter (620). The distal portion of rod portion (644) then engages the proximal end of marker (100). This forces marker (100) up ramp portion (628), which ejects marker (100) out of lateral aperture (626) and into the biopsy site. Although FIG. 3 shows marker (100) as including a carrier (120) and marker element (12) configuration, it should be understood that marker delivery device (600) may be readily used to deploy a marker (100) including only marker element (12) using the same procedures described herein.

After deployment of marker (100), an operator may confirm the positioning of marker (100) using ultrasonic visualization. After the positioning of marker (100) is confirmed, marker delivery device (600) can be removed and the patient can be sealed using conventional methods. In subsequent follow-up procedures, marker (100) can be further visualized using ultrasonic visualization.

III. EXEMPLARY DETACHABLE MARKER DELIVERY DEVICE

Figure 4:
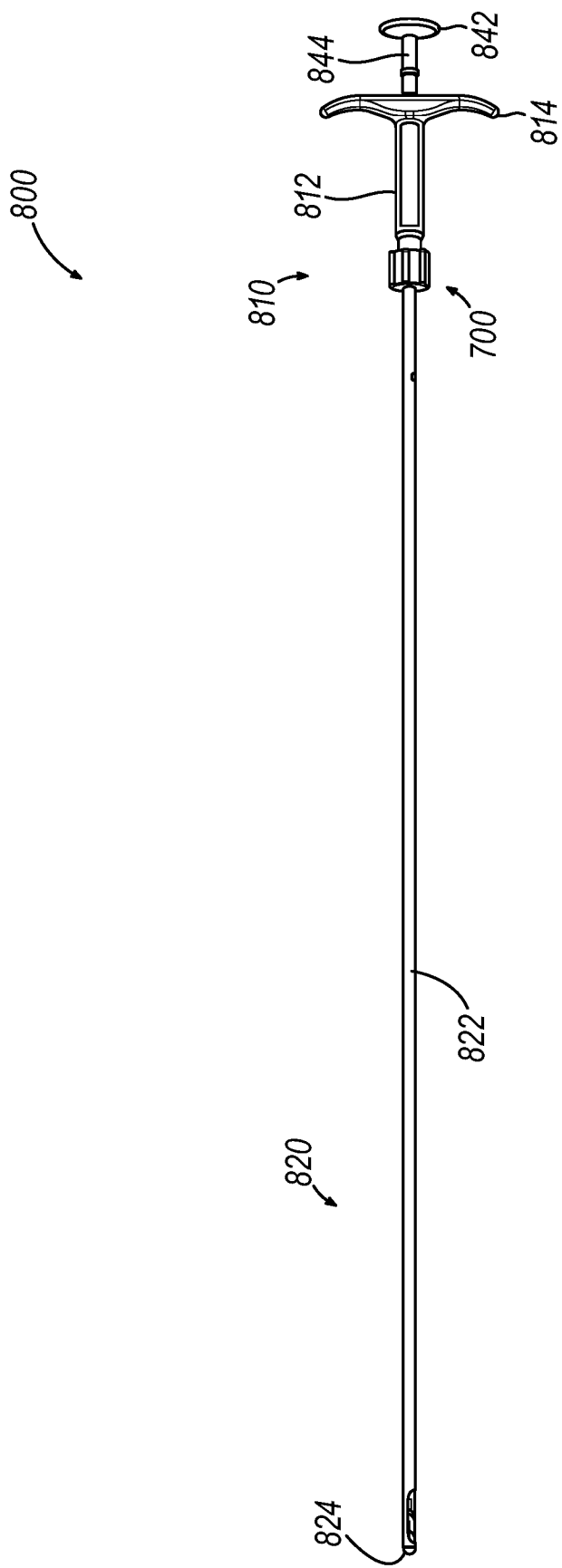
FIG. 4 depicts a side elevational view of another exemplary marker delivery device.

FIG. 4 shows an exemplary marker delivery device (800) that is substantially similar to marker delivery device (600) described above. As will be described in greater detail below, marker delivery device (800) can share many of the features and qualities with marker delivery device (600). However, unlike marker delivery device (600) described above, marker delivery device (800) of the present example includes a connection interface (700). As will be described in greater detail below, connection interface (700) is generally configured to permit separation of certain components of marker delivery device (800) to promote ease of use primarily through improved clearance between marker delivery device (800) and other components associated with a biopsy procedure. It should be understood that some examples of marker delivery device (800) may have other additional features as those of marker deliver device (600) or may delete some of the features disclosed above. The use of detachable marker delivery device (800) can allow for the use of interchangeable or common components across multiple marker product lines. Additionally, there may be customizable component combinations. In some examples, marker delivery device (800) and connection interface (700) can also be used to promote more efficient operation by combining reusable components with disposable components.

Figure 5:
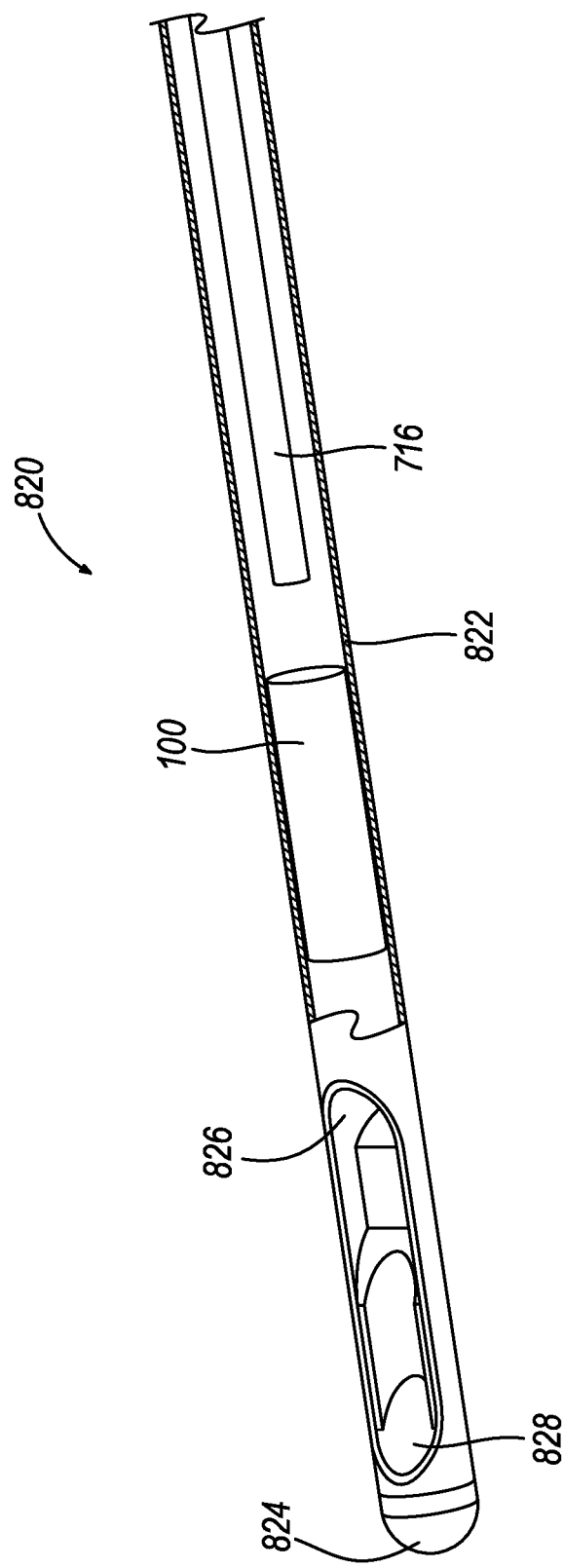
FIG. 5 depicts a perspective view of a marker application end of a cannula assembly of the marker delivery device of FIG. 4.

Like with marker delivery device (600) described above, marker delivery device (800) of the present example includes a delivery catheter (820) or elongate cannula configured to be inserted into or adjacent to a biopsy site through a biopsy needle, an introducer, or with just a bare delivery catheter (820). As with delivery catheter (620) described above, delivery catheter (820) of the present example comprises a cannula (822), a distal portion (824), a lateral aperture (826), and ramp portion (828). However, unlike delivery catheter (620), delivery catheter (820) of the present example includes a lower or distal push rod (716). Lower push rod (716) may also be characterized as a distal push rod. As best seen in FIG. 5, lower push rod (716) is located inside of a hollow interior of delivery catheter (820) and extends along the length thereof with the distal end of lower push rod (716) positioned near distal portion (824) of delivery catheter (820).

As best seen in FIG. 5, marker (100) can be placed inside of delivery catheter (820) before being inserted to the biopsy site. As will be described in greater detail below, lower push rod (716) is configured to translate distally toward distal portion (824) to thereby push marker (100) up ramp (826)

and out of lateral aperture (826). It should be understood that ramp (826) is merely optional and in some examples can be omitted. For instance, in some examples delivery catheter (820) can be of an "end deploy" configuration such that marker (100) is deployed through an open distal end in delivery catheter (820) rather than through a structure similar to lateral aperture (826). In such examples, ramp (826) can be omitted or substantially reduced in size so as to not entirely prevent deployment of marker (100).

Figure 6:
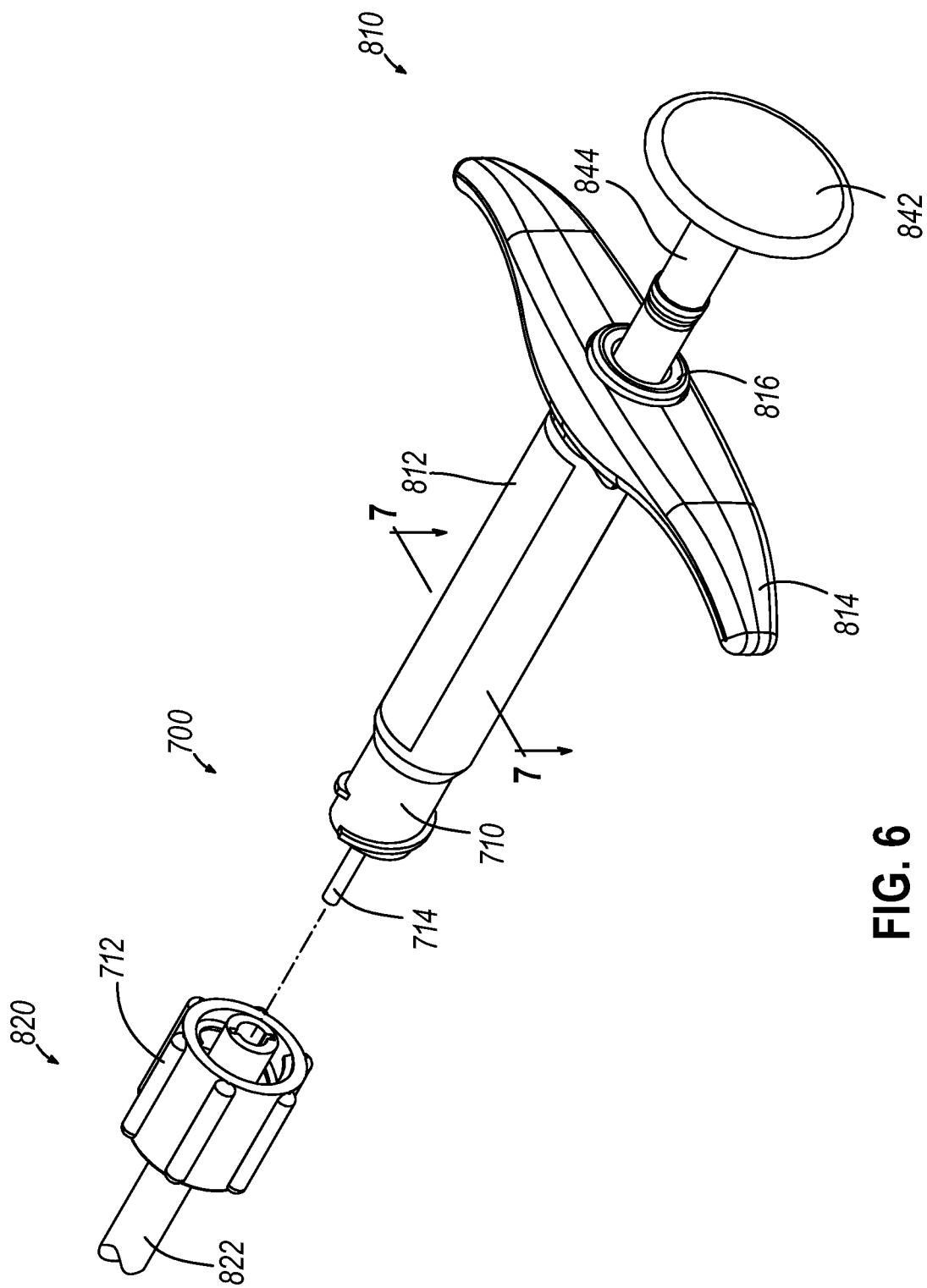
FIG. 6 depicts perspective view of an applicator and a connector interface of the marker delivery device of FIG. 4.
Figure 7:
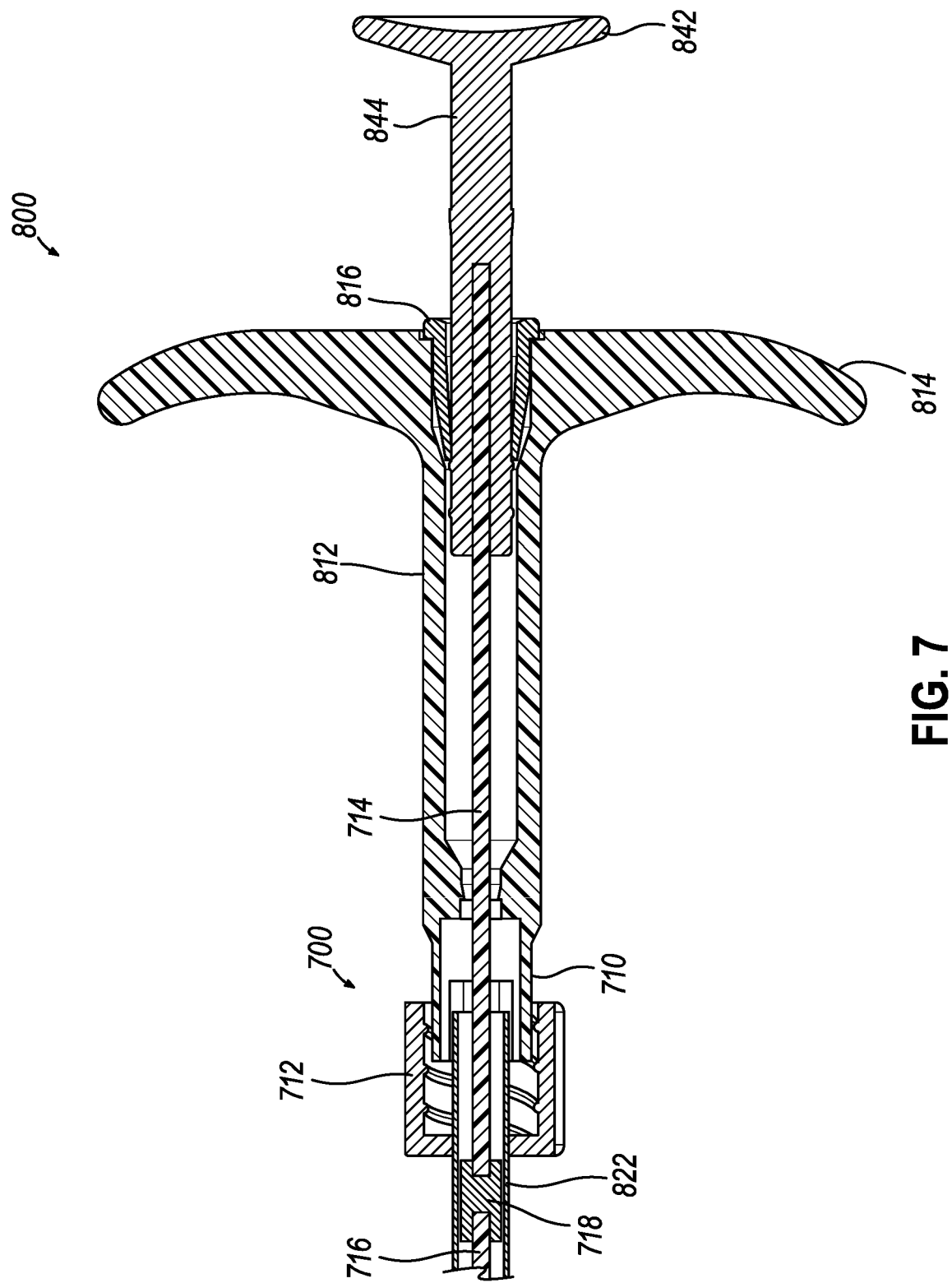
FIG. 7 depicts a cross-sectional view of the applicator and the cannula assembly lock of the marker delivery device of FIG. 4 along line 7-7 of FIG. 6.

Marker delivery device (800) of the present example further includes a handle assembly (810). As best seen in FIGS. 6 and 7, handle handle assembly (810) includes a body (812), a grip arm (814), a button portion (842), and a drive rod portion (844). Grip arm (814) extends outwardly from one or more sides of body (812) to enhance the ability of an operator to grip marker delivery device (800). Meanwhile, drive rod (844) extends proximally from a distal end of body (812). Button portion (842) is attached to a proximal end of drive rod (844). As will be described in greater detail below, drive rod (844) is configured to be translated within body (812) when force is applied to button portion (842). As best seen in FIG. 7, handle assembly (810) further includes a collar (816) or bushing that separates drive rod portion (844) from grip arm (814) and body (812).

As can also be seen, marker delivery device (800) includes connection interface (700) disposed between handle assembly (810) and delivery catheter (820). Connection interface (700) is generally configured to permit handle assembly (810) and delivery catheter (820) to selectively interlock and disengage from each other. It is contemplated that in one example, marker delivery device (800) can be provided already assembled together as one piece and can be detached at a later time. In another example, marker delivery device (800) may be provided in two separate pieces, handle assembly (810) and delivery catheter (820), and can be assembled when ready for use. It yet examples, marker delivery device (800) can be configured such that handle assembly (810) and delivery catheter (820) are fixedly attached together and inseparable or otherwise locked once the handle assembly (810) and delivery catheter (820) are attached together by connection interface (700).

As best seen in FIGS. 6 and 7, connection interface (700) includes a handle assembly lock (710) and a delivery catheter lock (712). Handle assembly lock (710) is located on handle assembly (810) and delivery catheter lock (712) is located on delivery catheter (820). In the example shown, handle assembly lock (710) and delivery catheter lock (712) are threaded couplers configured to engage each other, however they may be joined by any method available. In some examples, delivery catheter lock (712) is held to delivery catheter (820) by a protrusion or a flange protruding from the outer surface of delivery catheter (820). In other examples, delivery catheter lock (712) is integral with delivery catheter (820).

An upper or proximal push rod (714) is located inside of handle assembly (810) and translates when acted upon by button portion (842) as shown in FIG. 7, and transfers a push force to the lower push rod (716). Upper push rod can also be characterized as a proximal push rod. Upper push rod (714) is shown to extend through the length of body (812). The proximal end of upper push rod (714) is coupled to drive rod portion (844). As will be understood, this configuration permits button portion (842) to transfer translation to upper push rod (714) via drive rod portion (844). As shown in FIG. 7, the distal portion of upper push rod (714) extends through connection interface (700) when handle assembly lock (710) and a delivery catheter lock (712) are engaged.

Connection interface (700) further includes a push rod connection (718) configured to facilitate engagement between upper push rod (714) and lower push rod (716). In particular, Push rod connector (718) aligns and provides a point of contact between upper push rod (714) and lower push rod (716) and serves to keep lower push rod (716) from falling out of delivery catheter (820). Push rod connector (718) can be of any suitable configuration that allows for the upper push rod (714) and lower push rod (716) to engage with each other. Additionally, push rod connection (718) can be of any suitable configuration that also permits translation of upper push rod (714) to be transferred to lower push rod (716). By way of example only, in the present example, push rod connection (718) is a cylinder with a bore in both ends to accommodate each of lower push rod (716) and upper push rod (718), In the present example, push rod connector (718) is press fitted to the lower push rod (716) such that push rod connection (718) remains coupled to lower push rod (716), while upper push rod (718) can be removably coupled thereto. Upper push rod (714) may removably connect with push rod connector (718) so upper push rod (714) may disengage with push rod connector (718) when handle assembly lock (710) and delivery catheter lock (712) are separated. In some examples, push rod connector (718) may include a detent feature to facilitate the removable connection of the push rod connector (718) and the upper push rod (714).

In some examples, marker deliver device (800) can be equipped with a tactile feedback mechanism or plunger lock. For instance, collar (816) of marker delivery device (800) can include one or more interface features disposed within an interior of collar (816). Meanwhile, drive rod portion (844) can include one or more ribs configured to interact with the interface features of collar (816). Such ribs can be configured to provide tactile feedback during translation of drive rod portion (844) through interaction with interface features of collar (816). In addition, or in the alternative, the one or more ribs can be configured to selectively lock drive rod portion (844) at a given translational position through interaction with interface features of collar (816).

IV. EXEMPLARY METHOD OF DEPLOYING MARKER TO BIOPSY SITE

Figure 8A:
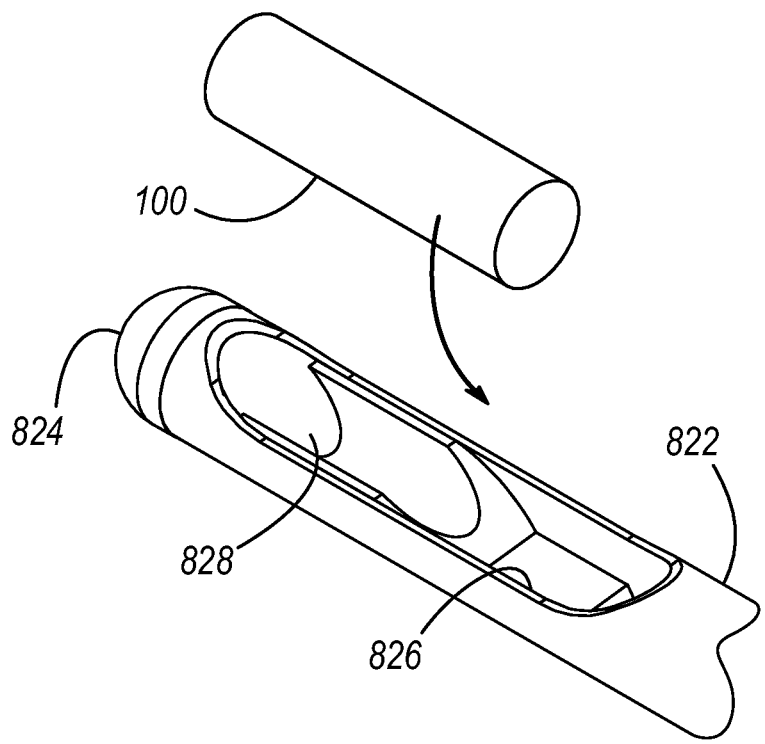
FIG. 8A depicts a detailed perspective view of the cannula assembly of FIG. 5, with a marker being inserted therein.

Referring now to FIGS. 8A-8D, a method of deploying a biopsy site marker (100) to a biopsy site is shown. As shown in FIG. 8A, the marker (100) is placed in cannula (822) of delivery catheter (820) through lateral aperture (826) near distal portion (824). Delivery catheter (820) may be provided separately from handle assembly (810) at this time to allow for ease of insertion of marker (100) into cannula (822). In some examples, delivery catheter (820) may be provided with marker (100) already placed inside of cannula (822). In some examples, delivery catheter (820) and handle assembly (810) may be provided together and marker (100) will be placed in cannula (822) after delivery catheter (820) and handle assembly (810) are attached. If both delivery catheter (820) and handle assembly (810) were disposable, providing both parts together is an efficient arrangement, so they could be disposed of after the procedure.

Figure 8B:
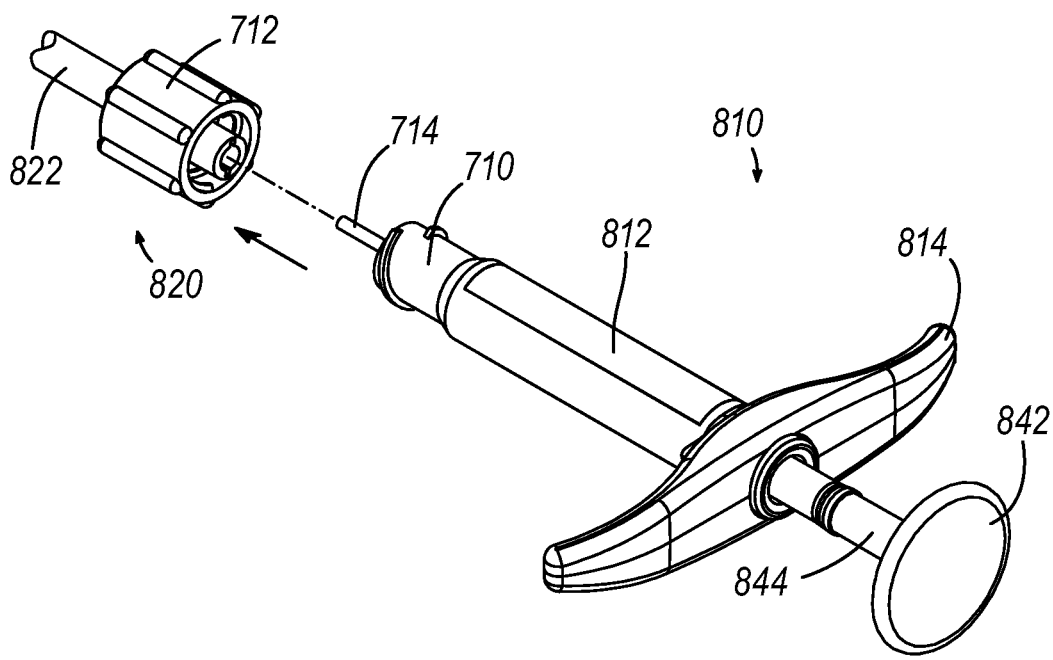
FIG. 8B depicts a detailed perspective view of the marker delivery device of FIG. 4, with a handle assembly being connected to the applicator of FIG. 7.
Figure 8C:
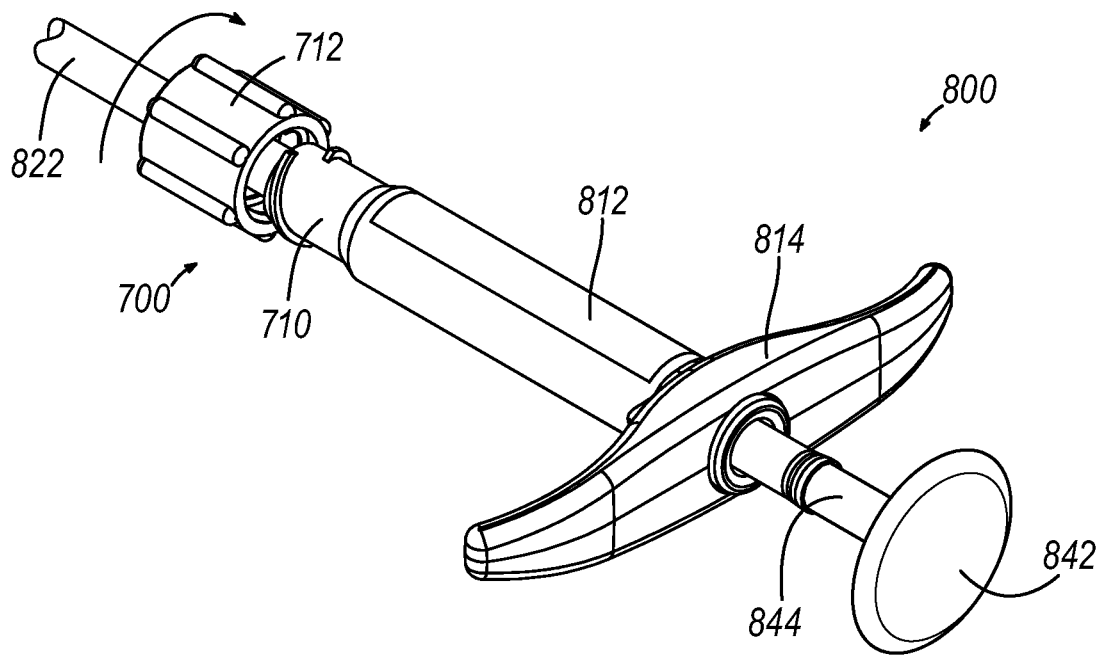
FIG. 8C depicts a detailed perspective view of the marker delivery device of FIG. 4, with the cannula assembly lock of FIG. 7 being actuated to connect the applicator.

FIG. 8B shows the steps of placing handle assembly (810) and delivery catheter (820) together. Handle assembly (810) and delivery catheter (820) are aligned along their lengths and attached at the ends having the handle assembly lock (710) and delivery catheter lock (712), so handle assembly lock (710) and delivery catheter lock (712) may engage. Upper push rod (714) may enter inside of delivery catheter lock (712) where it will attach to push rod connector (718). As shown in FIG. 8C, after handle assembly lock (710) and delivery catheter lock (712) are engaged, delivery catheter lock (712) may be turned or activated to surely connect with handle assembly lock (710) so that the two are rigidly connected wherein marker delivery device (800) may be inserted into the biopsy site without substantial bending or becoming disconnected. The action needed to be taken to rigidly connect handle assembly lock (710) and delivery catheter lock (712) depends on the type of engagement they require.

Figure 8D:
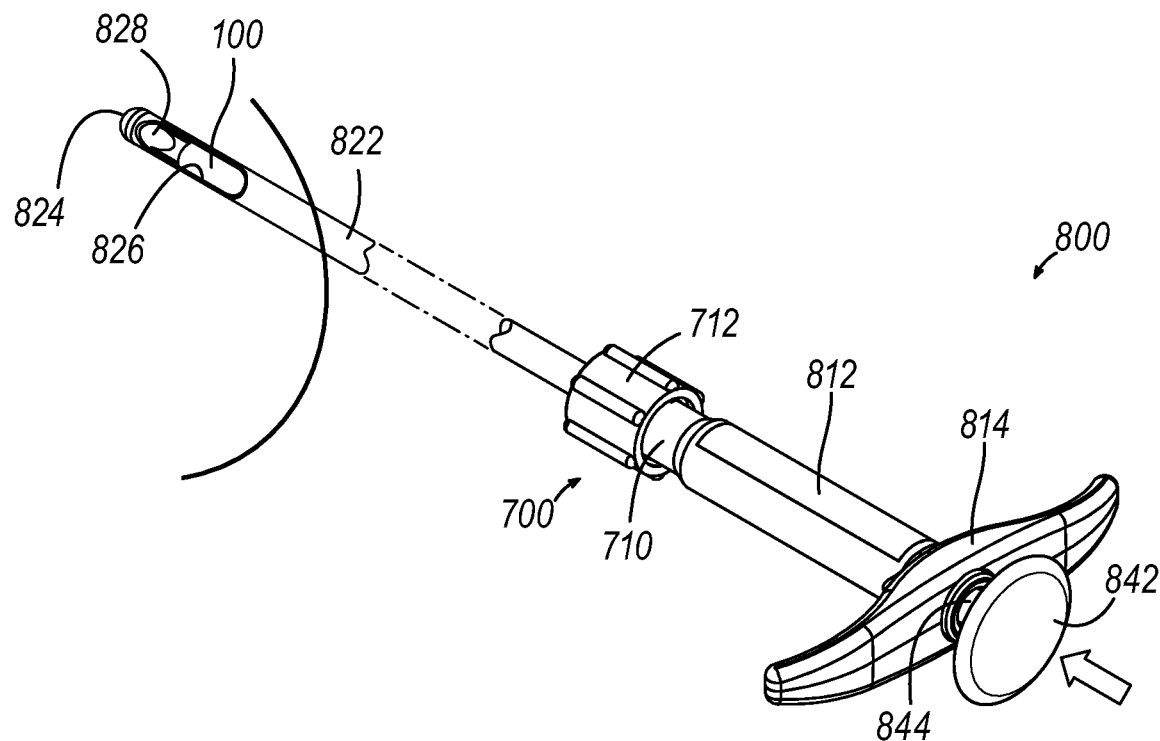
FIG. 8D depicts a perspective view of the marker delivery device of FIG. 4, with a button portion actuated to deploy a marker.

Delivery catheter (820) of the present example can next be inserted into the biopsy site, as is shown in FIG. 8D in order to deposit marker (100) in place. While delivery catheter (820) is inside the biopsy site, a force can be applied to button portion (842) so button portion (842) translates within body (812). As button portion (842) translates, it applies a force to upper push rod (714) which translates within body (842) and passes through connection interface (700). Upper push rod (714) then applies the force to push rod connector (718), which translates and applies the force to lower push rod (716). Lower push rod (716) then translates and applies the force to marker (100) which is released from cannula (822) and into the biopsy site. The user proceeds to mark the cavity in the same manner as they do today and perform any required testing and imaging. While delivery catheter (820) is in the patient, handle assembly (810) can be detached and reattached as needed. Handle assembly (810) may be detached by the user in order to significantly decrease any chance of collision with upright x-ray tube heads during post-marking imaging sequences of breast biopsy procedures, allow for the introduction of another handle assembly (810), or for any other reason needed that may occur during operation. The disengagement of handle assembly (810) from delivery catheter (820) can be performed by reversing the operation as shown in FIGS. 8B-8D. Such disengagement can occur at any suitable stage during a biopsy procedure. By way of example only, in one use, marker delivery device (800) can be inserted into a patient through a biopsy device. Next, handle assembly (810) can be removed to facilitate visualization of delivery catheter (820) to confirm positioning within the patient. Handle assembly (810) can then be reattached for marking. The operator may desire to detach the handle assembly (810) in order to prevent collision with another equipment near the marker delivery device (800), such as upright x-ray tube heads, or to ensure the operator themselves do not unintentionally collide with the handle assembly (810) after insertion. It may also be desirable to allow for separation of handle assembly (810) and delivery catheter (820) if they are disposable or interchangeable.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A marker delivery device comprising: a handle assembly having an upper push rod positioned within the handle assembly, wherein the upper push rod is adapted to translate inside the handle assembly; a delivery catheter adapted to be inserted into a biopsy site, the delivery catheter containing a marker, the delivery catheter having a lower push rod positioned within the delivery catheter and configured to engage the upper push rod, the lower push rod adapted to deploy the marker from the delivery catheter into the biopsy site through the discharge opening with the translation of the upper push rod; and a connection interface configured to removably attach the handle assembly with the delivery catheter and the upper push rod with the lower push rod.

Example 2

The marker delivery device of Example 1, wherein the handle assembly incudes a grip arm for manipulating the delivery device by hand.

Example 3

The marker delivery device of Examples 1 or 2, wherein the handle assembly further includes a button portion for translating the push rod with a finger.

Example 4

The marker delivery device of any one or more of Examples 1 through 3, wherein the handle assembly includes a collar between a portion of the handle assembly and the push rod.

Example 5

The marker delivery device of Example 4, wherein the collar includes ribs on the surface next to the button portion to provide tactile user feedback.

Example 6

The marker delivery device of any one or more of Examples 1 through 5, wherein the connection interface includes a delivery catheter lock and a hand assembly lock, wherein the delivery catheter lock and the handle assembly lock interlock.

Example 7

The marker delivery device of Example 6, wherein the delivery catheter lock and the handle assembly lock include a threaded interface.

Example 8

The marker delivery device of Example 1, wherein the connection interface includes a push rod connector to engage the upper push rod and the lower push rod.

Example 9

The marker delivery device of Example 8, wherein the push rod connector is press fitted to the lower push rod.

Example 10

The marker delivery device of Example 8, wherein the upper push rod is secured to the push rod connector with a dimple.

Example 11

The marker delivery device of any one or more of Examples 1 through 10, wherein the handle assembly is disposable.

Example 12

A marker delivery device comprising: a handle assembly having an proximal push rod positioned within the handle assembly, wherein the proximal push rod is adapted to translate inside the handle assembly; a delivery catheter adapted to be inserted into a biopsy site, the delivery catheter having a discharge opening containing a marker, the delivery catheter having a distal push rod positioned within the delivery catheter and configured to engage the proximal push rod, the distal push rod adapted to deploy the marker from the delivery catheter into the biopsy site through the discharge opening with the translation of the proximal push rod; and a connection interface configured to removably attach the handle assembly with the delivery catheter and the proximal push rod with the distal push rod.

Example 13

The marker delivery device of any one or more of Examples 1 through 12, wherein the delivery catheter is disposable.

Example 14

The marker delivery device of any one or more of Examples 1 through 10, 12 and 13, wherein the handle assembly is reusable.

Example 15

The marker delivery device of any one or more of Examples 1 through 12 and 14, wherein the delivery catheter is reusable.

Example 16

A marker delivery system comprising: a marker adapted for use in biopsy imaging; a delivery catheter including a delivery catheter lock, wherein the marker is contained within the delivery catheter; a detachable handle assembly including a handle assembly lock, wherein the handle assembly lock is configured to removably couple with the delivery catheter lock; and an upper push rod configured to couple to a lower push rod assembly when the delivery catheter lock is coupled with the handle assembly lock, wherein the upper push rod and the lower push rod deliver the marker from within the delivery catheter to the biopsy site.

Example 17

A method of delivering a marker to a biopsy location, the method comprising: loading the marker into a discharge opening of a delivery catheter, wherein the delivery catheter is adapted to be inserted into a biopsy site; removably attaching a handle assembly to the delivery catheter, wherein the handle assembly is adapted to deploy the marker; inserting the discharge opening into the biopsy site and delivering the marker to the biopsy site; removing the handle assembly from the delivery catheter and performing a post-marking imaging sequence; and reattaching the handle assembly to the delivery catheter and removing the delivery catheter from the biopsy site.

Example 18

The method of Example 17, wherein the delivery catheter and the handle assembly are packaged together.

Example 19

The method of Examples 17 or 18, wherein the marker is preloaded into the delivery catheter.

Example 20

The method of any one or more of Examples 17 through 19, wherein the delivery catheter and the handle assembly are disposable.

Example 21

A marker delivery device comprising: a handle having a grip and a plunger, wherein the plunger includes a distal extension; an elongate cannula having a hollow interior; a push rod, wherein the push rod is disposed within the hollow interior of the cannula, wherein the push rod is configured to translate within the hollow interior of the cannula; and a connector configured to removably fasten the handle to the cannula, wherein the distal extension of the plunger is configured to translate the push rod when the handle is fastened to the cannula with the connector.

Example 22

The marker delivery device of Example 21, wherein the handle includes a first fastener, wherein the cannula includes a second fastener, wherein the connector is configured to engage the first fastener and the second fastener to removably fasten the handle to the cannula.

Example 23

The marker delivery device of Example 22, wherein the first fastener includes threading.

Example 24

The marker delivery device of Example 23, wherein the connector includes threading that corresponds to the threading of the first fastener.

V. CONCLUSION

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A marker delivery device comprising:
   (a) a handle assembly having a body, a drive rod movable relative to the body, and a proximal push rod extending from the drive rod and positioned within the handle assembly, wherein the proximal push rod is adapted to translate inside the handle assembly;
   (b) a delivery catheter having an aperture and adapted to be inserted into a biopsy site, the delivery catheter containing a marker, the delivery catheter having a distal push rod positioned within the delivery catheter and configured to engage the proximal push rod, the distal push rod adapted to deploy the marker from the delivery catheter into the biopsy site through the aperture with the translation of the proximal push rod via the drive rod; and
   (c) a connection interface configured to removably attach the body of the handle assembly with the delivery catheter and the proximal push rod with the distal push rod at the position of the connection interface relative to the delivery catheter and the handle assembly, wherein the connection interface includes a delivery catheter lock and a handle assembly lock, wherein the delivery catheter lock and the handle assembly lock are configured to interlock to each other.

2. The marker delivery device of claim 1, wherein the handle assembly incudes a grip arm configured to permit manipulation of the marker delivery device by hand.

3. The marker delivery device claim 1, wherein the handle assembly further includes a button portion, wherein the button portion is in communication with the proximal push rod such that the button portion is configured to translate the proximal push rod.

4. The marker delivery device of claim 1, wherein the handle assembly further includes a collar disposed between a portion of the handle assembly and the proximal push rod.

5. The marker delivery device of claim 4, wherein the collar includes an interface portion configured to provide tactile feedback in response to translation of the button portion.

6. The marker delivery device of claim 1, wherein the delivery catheter lock and the handle assembly lock include a threaded interface.

7. The marker delivery device of claim 1, wherein the connection interface includes a push rod connector, wherein the push rod connector is configured to engage the distal push rod and the proximal push rod.

8. The marker delivery device of claim 7, wherein the push rod connector is press fitted to the distal push rod.

9. The marker delivery device of claim 7, wherein the proximal push rod is removably secured to the push rod connector.

10. The marker delivery device of claim 9, wherein the proximal push rod or the push rod connector includes a dimple, wherein the dimple is configured to removably secure the proximal push rod to the push rod connector.

11. The marker delivery device of claim 1, wherein the handle assembly is disposable.

12. The marker delivery device of claim 1, wherein the handle assembly is reusable.

13. The marker delivery device of claim 1, wherein the handle assembly is reusable, wherein the delivery catheter is disposable.

14. The marker delivery device of claim 1, wherein the handle assembly includes a first handle and a second handle, wherein each of the first handle and the second handle are configured to independently couple to the delivery catheter via the connection interface.

15. The marker delivery device of claim 1, wherein a distal portion of the proximal push rod extends through the connection interface when the handle assembly lock and delivery catheter lock are interlocked with each other.

* * * * *